US00PP12913P2

(12) United States Plant Patent
Moser

(10) Patent No.: US PP12,913 P2
(45) Date of Patent: Sep. 3, 2002

(54) CHRYSANTHEMUM PLANT NAMED 'ITALIA'

(75) Inventor: Frank Moser, Alva, FL (US)

(73) Assignee: Mozant, LLC, Oxnard, CA (US)

( * ) Notice: Subject to any disclaimer, the term of this patent is extended or adjusted under 35 U.S.C. 154(b) by 0 days.

(21) Appl. No.: 09/563,770

(22) Filed: May 1, 2000

(51) Int. Cl.[7] ..... A01H 5/00

(52) U.S. Cl. ..... Plt./297

(58) Field of Search ..... Plt./297

*Primary Examiner*—Bruce R. Campell
*Assistant Examiner*—Annette H. Para
(74) *Attorney, Agent, or Firm*—Christie, Parker & Hale, LLP

(57) ABSTRACT

A new plant variety of chrysanthemum producing pink daisy-type flowers with pink ray florets and yellow disc florets.

1 Drawing Sheet

BACKGROUND OF THE INVENTION

The present invention is directed to a new and distinct variety of *Chrysanthemum morifolium*. The varietal denomination of the new chrysanthemum is 'Italia'.

The new variety is a cross of two undistributed, unnamed, unpatented seedlings. The new variety has been asexually reproduced by vegetative cuttings in Ventura County, Calif. and the distinguishing characteristics are retained through successive generations of a sexual reproduction.

SUMMARY OF THE INVENTION

'Italia' is a chrysanthemum plant variety with daisy-type flowers having pink ray florets and yellow disc florets.

COMPARISON WITH OTHER VARIETY

The new variety has been shown to recover completely from a fully wilted condition without damage much better than a similar cultivar 'Empire Sweet Dreams' (U.S. Plant Pat. No. 11,908):

| | 'Empire Sweet Dreams' | 'ITALIA' |
|---|---|---|
| Inflorescence Diameter | About 7 cm | About 4 cm |
| Ray Floret coloration when mature | Near 48C | Near 42B |
| Plant height | About 28 cm | About 23 cm |
| Approximate quantity of inflorescence per stem | About 9 | About 15 |

BRIEF DESCRIPTION OF ILLUSTRATIONS

The accompanying photograph shows a typical specimens of the plant and flowers of the new variety with colors being as nearly true as possible with illustrations of this type.

DESCRIPTION OF THE PLANT

The following description of the new variety is of specimens grown in a greenhouse in Ventura County, Calif. The plants described are approximately 65 days old from a rooted cutting. 'Italia' has not been observed under all possible environmental conditions. The phenotype may vary with variations in the environment such as temperature, light intensity, day length and cultural conditions. The color designations herein are from The Royal Horticultural Society Colour Chart except where general terms are used.

To produce a commercial product the plants may be pinched once about 10 days after planting. No treatment with growth retardant was used with plants described. Useful growing conditions include average night temperatures of about 70° to 20° C., day temperatures of about 20° to 30° C. No susceptibility or resistance to disease has been observed. Resistance or susceptibility concerning insects has not been observed. Cold tolerance has not been observed.

Rooting characteristics:
- *Time to initiate roots.*—About 7 to 14 days at about 21° C.
- *Rooting habit.*—Fine, fibrous.

Plant:
- *Plant type.*—Herbaceous perennial.
- *Growth habit.*—Mounding.
- *Height.*—About 23 cm.
- *Growth rate.*—Moderate.
- *Branching characteristics.*—Free branching.

Foliage:
- *Arrangement.*—Alternate.
- *Compound or simple.*—Simple.
- *Quantity of leaves.*—Many.
- *Leaf size.*—Length: About 6 cm. Width: About 3 cm.
- *Leaf shape.*—General outline is ovate, shape palmately lobed.
- *Leaf tip.*—Acuminate.
- *Leaf base.*—Attenuate.
- *Leaf attachment.*—Stalked.
- *Petiole length.*—About 1.2 cm.
- *Margin type.*—Serrate.
- *Texture.*—Lightly pubescent.
- *Color.*—Young foliage upper side: Near 137B. Young foliage under side: Near 137C. Mature foliage upper side: Near 137A. Mature foliage under side: Near 137B.
- *Venation.*—Color: Venation upper side: Near 137B. Venation under side: Near 137D.

Bloom:

*Inflorescence.*—Flowering habit: Induced by darkness period greater than 13.5 hours; Approximately 50 days of day length required to induce and develop blooms. Inflorescence form: Daisy. Natural flowering season: Around the last 2 weeks in September. Quantity of inflorescence per stem: About 15. Inflorescence diameter: About 4 cm. Inflorescence depth: About 2 cm. Disc diameter: About 1.2 cm. Inflorescence longevity on plant: About 21 to 27 days. Persistence: Persistent.

*Ray florets.*—Appearance: Matte. Texture: Smooth. Number: About 50 to 60. Shape: Oblanceolate. Margin: Entire. Tip: Obtuse. Length: About 2.5 cm. Width: About 1 cm. Color: Upper side: First opening: Near 42A. Mature: Near 42B. Fading: Near 42C. Under side: First opening: Near 42B. Mature: Near 44D. Fading: Near 42D.

*Disc florets.*—Appearance: Shiny. Texture: Smooth. Number: About 100. Shape: Cylindric. Tip: Obtuse. Length: About 1 cm. Width: About 0.1 cm. Color: First opening: Near 14B. Mature: Near 13A. Fading: Near 17A.

*Peduncle.*—Length: Terminal, shortest: About 5 cm. Lateral, longest: About 7 cm. Color: Near 137C. Strength: Moderate. Habit: Erect.

*Inflorescence bud.* —Length: About 1 cm. Diameter: About 1.2 cm. Form or shape: Globular. Color: Near 42A.

*Involucral bracts.*—Length about 0.9 cm, width about 0.5 cm, shape ovate. Appearance: Matte. Texture: Lightly pubescent. Number: About 20 to 30. Shape: Ovate. Margin: Entire. Tip: Acute. Color: Upper side: Near 137B. Under side: Near 137B.

Reproductive organs:

*Ray florets.*—Pistillate: Pistil number: 1 per flower. Stigma shape: 2 branched. Stigma color: Near 7D. Style length: About 0.6 cm. Style color: Near 6D. Tip: Emarginated.

*Disc florets.*—Pistillate: Pistil number: 1 per flower. Stigma shape: Cylindric. Style length: About 1 cm.

*Staminate.*—Stamen number: About 5. Anther shape: Tubular. Anther color: Near 14C. Pollen color: Near 16A.

*Seeds.*—Seed production has not been observed.

What is claimed is:

1. A new and distinct chrysanthemum plant of the variety substantially as herein shown and described.

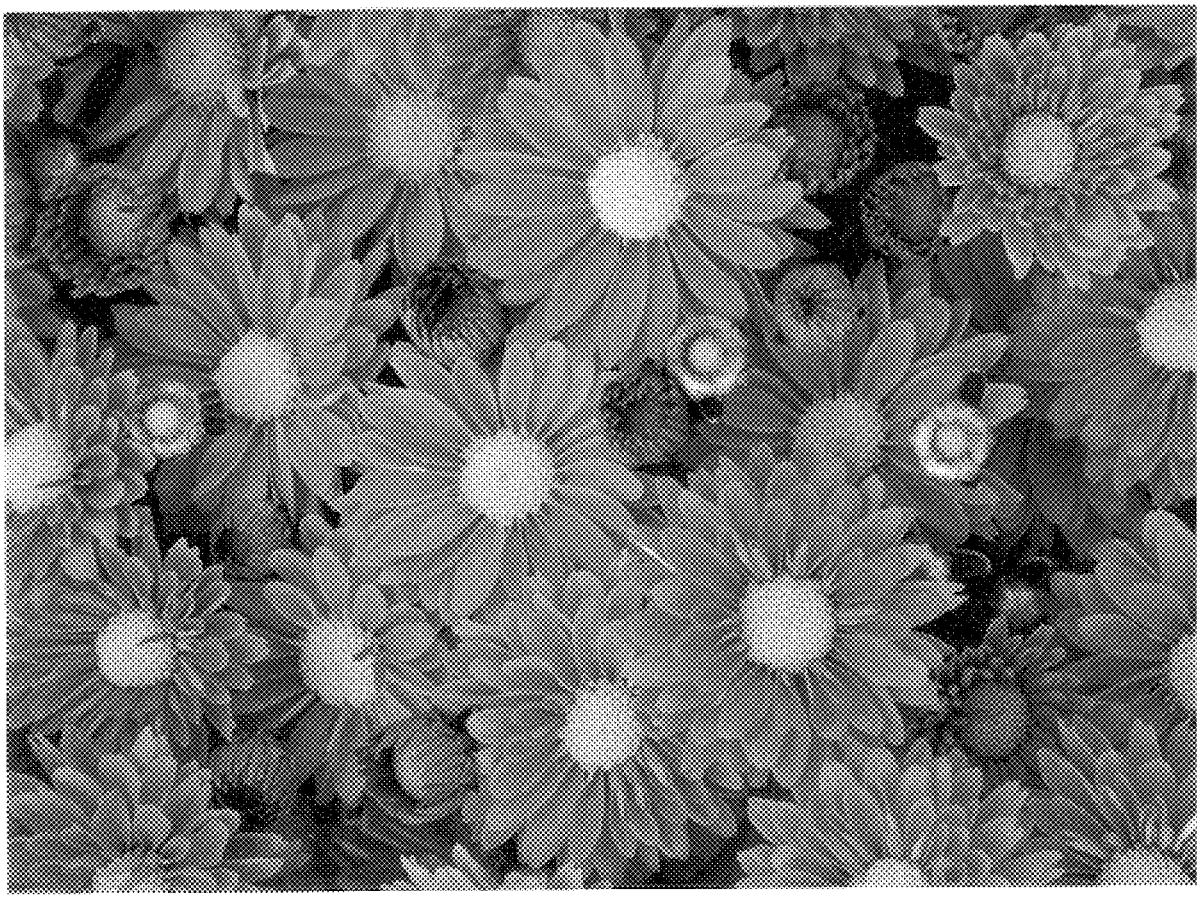

* * * * *